United States Patent
Papay

(10) Patent No.: US 11,712,565 B2
(45) Date of Patent: *Aug. 1, 2023

(54) SYSTEM AND METHOD FOR TREATING OBSTRUCTIVE SLEEP APNEA

(71) Applicant: The Cleveland Clinic Foundation, Cleveland, OH (US)

(72) Inventor: Francis A. Papay, Westlake, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/660,787

(22) Filed: Apr. 26, 2022

(65) Prior Publication Data

US 2022/0323752 A1 Oct. 13, 2022

Related U.S. Application Data

(60) Continuation of application No. 16/870,292, filed on May 8, 2020, now Pat. No. 11,338,142, which is a
(Continued)

(51) Int. Cl.
*A61N 1/36* (2006.01)
*A61N 1/372* (2006.01)
(Continued)

(52) U.S. Cl.
CPC .......... *A61N 1/3611* (2013.01); *A61F 2/2803* (2013.01); *A61N 1/0452* (2013.01);
(Continued)

(58) Field of Classification Search
CPC .................... A61N 1/3601; A61N 1/3611; A61N 1/36135; A61N 1/37223; A61N 1/0551;
(Continued)

(56) References Cited

U.S. PATENT DOCUMENTS 5,591,216 A 1/1997 Testerman et al.
5,988,171 A 11/1999 Sohn et al.
(Continued)

FOREIGN PATENT DOCUMENTS

WO WO 2007/080579 7/2007
WO WO 2007/080580 7/2007
(Continued)

OTHER PUBLICATIONS

Cienfuegos et al., Mandible—Surgical approach—Intraocular—AO Surgery Reference, v1.0 Dec. 1, 2008—(Accessed Apr. 18, 2016, Available at https://www2.aofoundation.org/wps/portal/surgery?showPage=approach&conten-tUrl=srg/91/04-Approaches/A12.sub.--intraoral.sub.--appr.sub.--ramus.sub.-- -cond.jsp&bone=CMF&segment=Mandible&approach=Intraoral).
(Continued)

*Primary Examiner* — Dinah Baria
(74) *Attorney, Agent, or Firm* — Levine Bagade Han LLP

(57) ABSTRACT

One aspect of the present disclosure relates to a system for treating obstructive sleep apnea in a subject. The system can include a power source and a neuromuscular stimulator in electrical communications with the power source. The neuromuscular stimulator can include a controller and at least one electrode. The controller can be configured to receive certain power and stimulation parameters associated with a therapy signal from the power source. The at least one electrode can be configured to deliver the therapy signal to a target tissue associated with control of a posterior base of the tongue of the subject.

20 Claims, 10 Drawing Sheets

Related U.S. Application Data continuation of application No. 15/618,199, filed on Jun. 9, 2017, now Pat. No. 10,675,467, which is a division of application No. 15/341,039, filed on Nov. 2, 2016, now Pat. No. 10,029,098, which is a division of application No. 14/547,400, filed on Nov. 19, 2014, now Pat. No. 9,757,560.

(60) Provisional application No. 61/994,149, filed on May 16, 2014, provisional application No. 61/905,989, filed on Nov. 19, 2013.

(51) Int. Cl.
*A61N 1/05* (2006.01)
*A61N 1/04* (2006.01)
*A61F 2/28* (2006.01)
*A61N 1/378* (2006.01)

(52) U.S. Cl.
CPC ......... *A61N 1/0456* (2013.01); *A61N 1/0551* (2013.01); *A61N 1/3601* (2013.01); *A61N 1/36135* (2013.01); *A61N 1/3787* (2013.01); *A61N 1/37223* (2013.01); *A61F 2002/2807* (2013.01)

(58) Field of Classification Search
CPC .. A61N 1/3787; A61N 1/0452; A61N 1/0456; A61F 2/2803; A61F 2002/2807
See application file for complete search history.

(56) References Cited

U.S. PATENT DOCUMENTS

| | | | |
|---|---|---|---|
| 6,240,316 B1 | 5/2001 | Richmond et al. |
| 6,770,022 B2 | 8/2004 | Mechlenburg et al. |
| 7,660,632 B2 | 2/2010 | Kirby et al. |
| 7,885,713 B2 | 2/2011 | Campbell et al. |
| 8,498,712 B2 | 7/2013 | Bolea et al. |
| 8,574,164 B2 | 11/2013 | Mashiach |
| 8,577,464 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,585,617 B2 | 11/2013 | Mashiach et al. |
| 8,588,941 B2 | 11/2013 | Mashiach |
| 8,626,304 B2 | 1/2014 | Bolea et al. |
| 8,644,957 B2 | 2/2014 | Mashiach |
| 8,700,183 B2 | 4/2014 | Mashiach |
| 8,718,776 B2 | 5/2014 | Mashiach et al. |
| 8,744,589 B2 | 6/2014 | Bolea et al. |
| 8,751,005 B2 | 6/2014 | Meadows et al. |
| 8,798,773 B2 | 8/2014 | Mashiach |
| 8,812,113 B2 | 8/2014 | Mashiach |
| 8,812,135 B2 | 8/2014 | Mashiach |
| 8,831,730 B2 | 9/2014 | Mashiach et al. |
| 8,838,256 B2 | 9/2014 | Mashiach et al. |
| 8,897,880 B2 | 11/2014 | Mashiach |
| 8,897,895 B2 | 11/2014 | Mashiach |
| 8,903,493 B2 | 12/2014 | Mashiach et al. |
| 8,903,515 B2 | 12/2014 | Mashiach |
| 8,948,871 B2 | 2/2015 | Mashiach et al. |
| 8,958,893 B2 | 2/2015 | Mashiach |
| 8,989,868 B2 | 3/2015 | Mashiach et al. |
| 9,031,653 B2 | 5/2015 | Mashiach |
| 9,031,654 B2 | 5/2015 | Meadows et al. |
| 9,044,612 B2 | 6/2015 | Mashiach |
| 9,061,151 B2 | 6/2015 | Mashiach et al. |
| 9,061,162 B2 | 6/2015 | Mashiach et al. |
| 9,095,725 B2 | 8/2015 | Mashiach |
| 9,101,774 B2 | 8/2015 | Mashiach et al. |
| 9,155,899 B2 | 10/2015 | Mashiach et al. |
| 9,220,907 B2 | 12/2015 | Mashiach et al. |
| 9,220,908 B2 | 12/2015 | Mashiach |
| 9,248,290 B2 | 2/2016 | Mashiach |
| 9,248,291 B2 | 2/2016 | Mashiach |
| 9,248,302 B2 | 2/2016 | Mashiach et al. |
| 9,302,093 B2 | 4/2016 | Mashiach |
| 9,308,370 B2 | 4/2016 | Lima et al. |
| 9,308,381 B2 | 4/2016 | Mashiach et al. |
| 9,314,613 B2 | 4/2016 | Mashiach |
| 9,314,641 B2 | 4/2016 | Meadows et al. |
| 9,327,132 B2 | 5/2016 | Mashiach |
| 9,339,651 B2 | 5/2016 | Meadows et al. |
| 9,358,392 B2 | 6/2016 | Mashiach |
| 9,393,435 B2 | 7/2016 | Mashiach |
| 9,403,025 B2 | 8/2016 | Mashiach et al. |
| 9,409,013 B2 | 8/2016 | Mashiach et al. |
| 9,415,215 B2 | 8/2016 | Mashiach |
| 9,415,216 B2 | 8/2016 | Mashiach |
| 9,421,372 B2 | 8/2016 | Mashiach et al. |
| 9,463,318 B2 | 10/2016 | Mashiach et al. |
| 2002/0010495 A1 | 1/2002 | Freed |
| 2006/0224211 A1 | 10/2006 | Durand |
| 2007/0160274 A1 | 7/2007 | Mashiach |
| 2007/0263915 A1 | 11/2007 | Mashiach |
| 2008/0260217 A1 | 10/2008 | Mashiach |
| 2009/0082831 A1 | 3/2009 | Paul et al. |
| 2009/0226057 A1 | 9/2009 | Mashiach et al. |
| 2010/0094379 A1 | 4/2010 | Meadows |
| 2010/0241195 A1 | 9/2010 | Meadows et al. |
| 2011/0093036 A1 | 4/2011 | Mashiach |
| 2011/0125212 A1 | 5/2011 | Tyler |
| 2011/0230702 A1 | 9/2011 | Honour |
| 2012/0010532 A1 | 1/2012 | Bolea et al. |
| 2013/0085537 A1 | 4/2013 | Mashiach |
| 2013/0204097 A1 | 8/2013 | Rondoni et al. |
| 2013/0289401 A1 | 10/2013 | Colbaugh et al. |
| 2014/0031840 A1 | 1/2014 | Mashiach |
| 2014/0031902 A1 | 1/2014 | Mashiach et al. |
| 2014/0031903 A1 | 1/2014 | Mashiach |
| 2014/0031904 A1 | 1/2014 | Mashiach |
| 2014/0046221 A1 | 2/2014 | Mashiach et al. |
| 2014/0052219 A1 | 2/2014 | Mashiach et al. |
| 2014/0100642 A1 | 4/2014 | Mashiach |
| 2014/0135868 A1 | 5/2014 | Bashyam |
| 2014/0172061 A1 | 6/2014 | Mashiach |
| 2014/0358026 A1 | 12/2014 | Mashiach et al. |
| 2014/0358189 A1 | 12/2014 | Mashiach et al. |
| 2014/0358196 A1 | 12/2014 | Mashiach |
| 2014/0371802 A1 | 12/2014 | Mashiach et al. |
| 2014/0371817 A1 | 12/2014 | Mashiach et al. |
| 2015/0032177 A1 | 1/2015 | Mashiach et al. |
| 2015/0112402 A1 | 4/2015 | Mashiach |
| 2015/0112416 A1 | 4/2015 | Mashiach et al. |
| 2015/0265221 A1 | 9/2015 | Flanagan et al. |
| 2015/0290465 A1 | 10/2015 | Mashiach |
| 2015/0343221 A1 | 12/2015 | Mashiach |
| 2016/0121121 A1 | 5/2016 | Mashiach |
| 2016/0121122 A1 | 5/2016 | Mashiach |
| 2016/0175587 A1 | 6/2016 | Lima et al. |
| 2016/0184583 A1 | 6/2016 | Meadows et al. |
| 2016/0235990 A1 | 8/2016 | Mashiach |
| 2016/0346537 A1 | 12/2016 | Mashiach |
| 2020/0269044 A1 | 8/2020 | Papay |

FOREIGN PATENT DOCUMENTS

| | | |
|---|---|---|
| WO | WO 2008/129545 | 10/2008 |
| WO | WO 2009/007896 | 1/2009 |
| WO | WO 2009/109971 | 9/2009 |
| WO | WO 2011/048590 | 4/2011 |
| WO | WO 2011/077433 | 6/2011 |
| WO | WO 2013/046032 | 4/2013 |
| WO | WO 2013/046035 | 4/2013 |
| WO | WO 2013/046038 | 4/2013 |
| WO | WO 2013/046039 | 4/2013 |
| WO | WO 2013/046040 | 4/2013 |
| WO | WO 2013/046042 | 4/2013 |
| WO | WO 2013/046043 | 4/2013 |
| WO | WO 2013/046044 | 4/2013 |

(56) References Cited

FOREIGN PATENT DOCUMENTS

| | | |
|---|---|---|
| WO | WO 2013/046048 | 4/2013 |
| WO | WO 2013/046049 | 4/2013 |
| WO | WO 2013/046053 | 4/2013 |
| WO | WO 2013/057597 | 4/2013 |
| WO | WO 2013/061169 | 5/2013 |
| WO | WO 2014/016684 | 1/2014 |
| WO | WO 2014/016686 | 1/2014 |
| WO | WO 2014/016687 | 1/2014 |
| WO | WO 2014/016688 | 1/2014 |
| WO | WO 2014/016691 | 1/2014 |
| WO | WO 2014/016692 | 1/2014 |
| WO | WO 2014/016693 | 1/2014 |
| WO | WO 2014/016694 | 1/2014 |
| WO | WO 2014/016697 | 1/2014 |
| WO | WO 2014/016700 | 1/2014 |
| WO | WO 2014/016701 | 1/2014 |
| WO | WO 2014/049448 | 4/2014 |
| WO | WO 2014/057361 | 4/2014 |
| WO | WO 2014/096969 | 6/2014 |
| WO | WO 2014/096971 | 6/2014 |
| WO | WO 2014/096973 | 6/2014 |
| WO | WO 2014/207576 | 12/2014 |
| WO | WO 2015/004540 | 1/2015 |

OTHER PUBLICATIONS

Cienfuegos et al., Mandible—Surgical approach—Intraocular—AO Surgery Reference, v1.0 Dec. 1, 2008—(Accessed Apr. 18, 2016, Available at https://www2.aofoundation.org/wps/portal/surgery?showPage=approach&conten-tUrl=srg/91/04-Approaches/A50_Submental.jsp&bone=CMF&segment=Mandible&approach=Submental).

Schwartz, Alan R., et al. "Electrical stimulation of the lingual musculature in obstructive sleep apnea." Journal of Applied Physiology 81.2 (1996): 643-652.

SYSTEM AND METHOD FOR TREATING OBSTRUCTIVE SLEEP APNEA

RELATED APPLICATIONS

This application is a continuation of U.S. patent application Ser. No. 16/870,292 filed May 8, 2020, which is a continuation of U.S. patent application Ser. No. 15/618,199 filed Jun. 9, 2017 (now U.S. Pat. No. 10,675,467), which is a divisional of U.S. patent application Ser. No. 15/341,039 filed Nov. 2, 2016 (now U.S. Pat. No. 10,029,098), which is a divisional of U.S. patent application Ser. No. 14/547,400 filed Nov. 19, 2014 (now U.S. Pat. No. 9,757,560), which claims priority to U.S. Provisional Patent Application Serial Nos. 61/905,989, filed Nov. 19, 2013, and 61/994,149, filed May 16, 2014, the entirety of each of which is hereby incorporated by reference for all purposes.

TECHNICAL FIELD

The present disclosure relates generally to a system and method for treating sleep disorders and, more particularly, to a system and method for treating obstructive sleep apnea.

BACKGROUND

Preterm Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc. Continuous positive airway pressure (CPAP) is a standard treatment for OSA. While CPAP is non-invasive and highly effective, it is not well tolerated by patients. Patient compliance for CPAP is often reported to be between 40% and 60%. Surgical treatment options for OSA, such as anterior tongue muscle repositioning, orthognathic bimaxillary advancement, uvula-palatal-pharyngoplasty, and tracheostomy are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibulary advancement), and/or they may be socially stigmatic (e.g., tracheostomy) and extensive morbidity.

SUMMARY

The present disclosure relates generally to a system and methods for treating sleep disorders and, more particularly, to a system and methods for treating obstructive sleep apnea (OSA).

One aspect of the present disclosure relates to a system for treating OSA in a subject. The system can comprise a power source and a neuromuscular stimulator in electrical communication with the power source. The neuromuscular stimulator can include a controller and at least one electrode. The controller can be configured to receive certain power and stimulation parameters associated with a therapy signal from the power source. The at least one electrode can be configured to deliver the therapy signal to a target tissue associated with control of a posterior base and lingual positioning of the tongue of the subject.

Another aspect of the present disclosure relates to a method for treating OSA in a subject. One step of the method can include providing a system comprising a power source and a neuromuscular stimulator in electrical communication with the power source. The neuromuscular stimulator can include a controller and at least one electrode. The controller can be configured to receive certain power and stimulation parameters associated with a therapy signal from the power source. Next, the neuromuscular stimulator can be implanted in the subject so that the at least one electrode is in electrical communication with a target tissue associated with direct or indirect control of a posterior base of the tongue and posterior oropharyngeal airway of the subject. The power source can then be activated so that the therapy signal is delivered to the at least one electrode for a time and in an amount sufficient to open the oropharyngeal airway to the laryngeal introitus.

Another aspect of the present disclosure relates to a method for treating OSA in a subject. One step of the method can include providing a closed-loop system comprising a power source, a neuromuscular stimulator, and a sensing component. The neuromuscular stimulator can be in electrical communication with the power source. The neuromuscular stimulator can include a controller and at least one electrode. The controller can be configured to receive certain power and stimulation parameters associated with a therapy signal from the power source. The sensing component can be configured to detect at least one physiological parameter or a related symptom associated with OSA. Next, the system can be implanted in the subject so that the at least one electrode and the sensing component are in electrical communication with first and second target tissues, respectively, associated with direct or indirect control of a posterior base of the tongue and posterior oropharyngeal airway of the subject. A sensor signal can then be generated by the sensing component based on a detected at least one physiological parameter or a related symptom associated with OSA. The controller can activate the neuromuscular stimulator to adjust application of the therapy signal to the first target tissue in response to the sensor signal to treat the OSA.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Unless defined otherwise, all technical and scientific terms used herein have the same meaning as is commonly understood by one of skill in the art to which the present disclosure pertains.

In the context of the present disclosure, the terms "modulate" or "modulating" can refer to causing a change in neuronal and/or muscle activity, chemistry, and/or metabolism. The change can refer to an increase, decrease, or even a change in a pattern of neuronal and/or muscle activity. The terms may refer to either excitatory or inhibitory stimulation, or a combination thereof, and may be at least electrical, magnetic, optical or chemical, or a combination of two or more of these.

As used herein, the term "electrical communication" can refer to the ability of an electric field generated by an electrode or electrode array to be transferred, or to have a neuromodulatory effect, within and/or on a target tissue, such as a muscle or nerve.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "obstructive sleep apnea" or "OSA" can refer to a breathing disorder that occurs primarily during sleep with consequences that may persist throughout the waking hours in the form of sleepiness. OSA can be characterized by periodic collapse of the upper airway during sleep with apneas, hypopneas, or a continuous or sustained reduction in ventilation and excessive daytime sleepiness, neurocognitive defects and depression.

As used herein, the term "treating" can refer to therapeutically regulating, preventing, improving, alleviating the signs and symptoms of, and/or reducing the effects of a sleeping disorder, such as OSA and oropharyngeal airway obstruction. The term can also refer to chronic or acute treatment.

As used herein, the term "therapy signal" can refer to an electrical and/or chemical signal that is delivered to a target tissue and is capable of modulating (e.g., electrically modulating) the target tissue and/or a bodily organ (e.g., a tongue) associated with the target tissue.

When an element or structure is referred to herein as being "on," "engaged to," "connected to," "attached to", or "coupled to" another element or structure, it may be directly on, engaged, connected or coupled to the other element or structure, or intervening elements or structures may be present. In contrast, when an element is referred to as being "directly on," "directly engaged to," "directly connected to," or "directly coupled to" another element or structure, there may be no intervening elements or structures present. Other words used to describe the relationship between elements should be interpreted in a like fashion (e.g., "between" versus "directly between," "adjacent" versus "directly adjacent," etc.).

Overview

Figure 1:
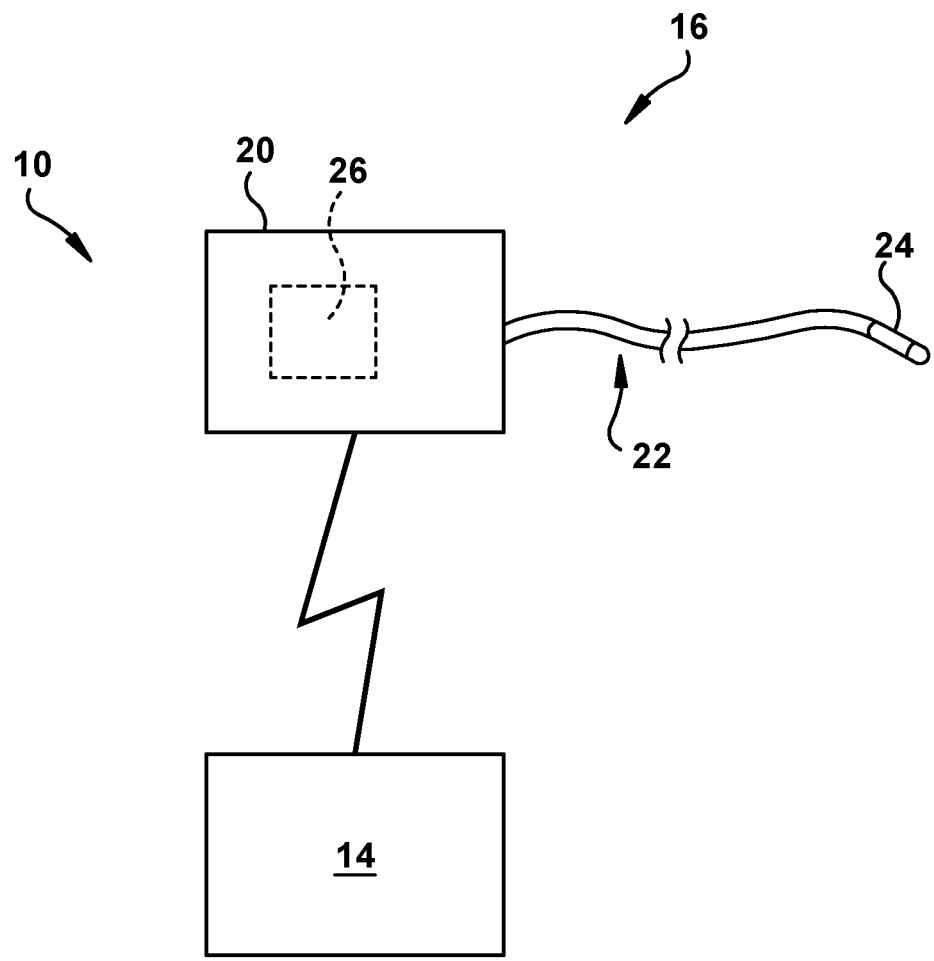
FIG. 1 is a schematic illustration of a system for treating obstructive sleep apnea (OSA) constructed in accordance with one aspect of the present disclosure.

The present disclosure relates generally to a system and method for treating sleep disorders and, more particularly, to a system and method for treating OSA. As shown in FIG. 1, one aspect of the present disclosure can include a system 10 for treating a sleeping disorder, such as OSA. OSA affects almost every system in the body and, in some individuals, can result in increased incidence of cardiovascular disease. As discussed in more detail below, the present disclosure provides a minimally invasive, implantable system 10 configured to modulate one or more muscles of the anterior lingual musculature 12 (FIG. 8) and thereby open airflow and prevent or mitigate obstruction during sleep. Advantageously, the present disclosure helps to minimize the deleterious effects of OSA on the day-to-day life of individuals suffering from OSA, as well as preventing or mitigating stress on certain muscles that are being unnecessarily stimulated as a result of OSA. Such advantages are realized, at least in part, because: (1) only a single surgical site is required for implantation of the system 10; (2) the system can be configured for highly selective stimulation of one or more muscles comprising the anterior lingual musculature; (3) dissection of the hypoglossal nerve trunk is not required to practice the present disclosure; (4) implantation of the system does not produce any visible scarring; and (5) once implanted, subjects cannot see, feel, or sense the presence of the system.

System

In one aspect, the present disclosure can include a system 10 (FIG. 1) for treating OSA in a subject. The system 10 can comprise a power source 14 in electrical communication with a neuromuscular stimulator 16. The power source 14 and the neuromuscular stimulator 16 can be in direct and/or indirect electrical communication with one another. In some instances, the power source 14 and the neuromuscular stimulator 16 can be in direct electrical communication with one another via one or more wires (not shown). In other instances, the power source 14 and the neuromuscular stimulator 16 can be in indirect electrical communication with one another (e.g., via a wireless link). The system 10 can be portable and adapted to be borne by a subject suffering from OSA for a desired period of time. In some instances, the system 10 can be borne by a subject for an acute period of time (e.g., during an emergency situation), for a semi-chronic period of time (e.g., less than about a week to about 6 weeks), or for a chronic period of time (e.g., greater than about 6 weeks). For example, the neuromuscular stimulator 16 can be temporarily or permanently implanted within, on, or otherwise associated with a subject suffering from OSA.

In another aspect, the power source 14 can be configured to deliver a therapy signal having certain power and stimulation parameters to the neuromuscular stimulator 16. Examples of such power and stimulation parameters can include the pulse waveform, the signal pulse width, the signal pulse frequency, the signal pulse phase, the signal pulse polarity, the signal pulse amplitude, the signal pulse intensity, and the signal pulse duration of the therapy signal. The power source 14 can be capable of conveying a variety of currents and voltages to the neuromuscular stimulator 16. In some instances, the power source 14 can communicate stimulating energy, such as electrical current pulses to the neuromuscular stimulator. The power source 14 can optionally include circuitry and/or other implantable components for outputting electrical pulses to the neuromuscular stimulator 16. Signals from the power source 14 can additionally or optionally be communicative in nature, for example, communicating stimulation program information, subject information, and other types of information. In some instances, the power source 14 is located external to the subject and in electrical communication with the neuromuscular stimulator 16 via inductive coupling. For example, the power source 14 can be configured as part of a wearable device, such as a chin strap 18 (FIG. 2), which may be worn at bedtime. In such instances, the power source 14 is not physically "wired" to the neuromuscular stimulator 16 (FIG. 1).

In another aspect, the neuromuscular stimulator 16 can include any active implantable medical device configured for implantation for a relatively short or long period of time. As shown in FIG. 1, the neuromuscular stimulator 16 can include a housing 20 connected to one or more electrical leads 22 having at least one electrode 24 associated therewith. Various electrical components, such as a controller 26, can be hermetically sealed and contained within the housing 20. As discussed in more detail below, all or only a portion of the neuromuscular stimulator 16 can be configured for implantation on or in the mandible of a subject. For example, all or only a portion of the neuromuscular stimulator 16 can be configured for implantation on, in, or through a mandible 28 (e.g., the mentum 29) (FIG. 8) of the subject.

The controller 26 (FIG. 1) can be configured to receive the power and stimulation parameters associated with a therapy signal from the power source 14. In some instances, the controller 26 can include a microprocessor (not shown), a hardwired circuit (not shown), or other appropriate means for controlling various aspects of the system 10. For example, the controller 26 can operate the power source 14, convey therapy signals to the at least one electrode 24, and/or receive information from various sources, such as the at least one electrode or a sensor (not shown). The controller 26 can be configured to store a stimulation program (or programs) and operate the power source 14 according to the stimulation program(s). Stimulation programs can include predetermined, set programs (e.g., hardwired into the controller) and adaptive, dynamic programs (e.g., software that adapts an artificial stimulation pattern according to various inputs). The controller 26 can select between various programs and/or actively modify a stimulation program according to various inputs, such as information received from a subject, information received from a sensor, information received from the power source 14, information received from the at least one electrode 24, and/or information received from a health care provider.

In another aspect, the lead 22 of the neuromuscular stimulator 16 can include at least one electrode 24 that is in electrical communication with the controller 26. The at least one electrode 24 can be configured to deliver a therapy signal to a target tissue associated with direct or indirect control of a posterior base of the tongue of a subject. In further describing representative electrodes 24, which are described in the singular, it will be apparent that more than one electrode may be used as part of the system 10. Accordingly, the description of a representative electrode 24 suitable for use in the system 10 of the present disclosure is applicable to other electrodes that may be employed.

The electrode 24 can include one or more of the following types and/or categories of electrodes: epimysial electrodes; intramuscular electrodes, such as Peterson electrodes; nerve cuff electrodes; self-contained electrodes; monopolar electrodes; bipolar electrodes; multi-contact electrodes; and/or other known electrode types/categories and combinations thereof. It will be appreciated that the electrode 24 can include one or more associated flexible, extensible electrical leads 22. The lead 22 and/or the electrode 24 can be highly flexible so as to not hinder regular tongue movement. In some instances, all or only a portion of the lead 22 can include one or more deployable anchoring elements (not shown) (e.g., barbs, hooks, etc.). The anchoring element(s) can be selectively retractable and extendable. The anchoring element(s) facilitate secure placement of the lead 22 (and thus the electrode 24) in or about a target tissue, such as a muscle, which is under constant flexion and relaxation.

The electrode 24 can be controllable to provide therapy signals that may be varied in voltage, frequency, pulse-width, current and/or intensity. For example, the electrode 24 can also provide both positive and negative current flow from the electrode and/or be capable of stopping current flow from the electrode and/or changing the direction of current flow from the electrode. In some instances, the electrode 24 has the capacity for variable output, linear output and short pulse-width. In other instances, the electrode 24 can comprise a coil configured to deliver magnetic stimulation. The electrode 24 may be mono-polar, bipolar or multi-polar. To minimize the risk of an immune response triggered by the subject against certain components of the neuromuscular stimulator 16, and also to minimize damage thereto (e.g., corrosion from other biological fluids, etc.), the electrode 24 (and any wires and optional housing materials) can be made of inert materials, such as silicon, metal, plastic and the like. In other instances, the electrode 24 can be a multi-vector electrode capable of directing current to different muscles of anterior lingual musculature 12. In further instances, the system 10 can include more than one electrode 24, such as an array of electrodes to stimulate a field of arborizing hypoglossal branches associated with a particular target muscle (or group of muscles).

In another aspect, the system 10 can be configured as an open-loop or closed-loop system. In an open-loop system, for example, a physician or the subject may, at any time, manually or by the use of pumps, motorized elements, etc., adjust treatment parameters of the system 10. Alternatively, in a closed-loop system (discussed below), treatment parameters (e.g., electrical signals) may be automatically adjusted in response to a sensed physiological parameter or a related symptom indicative of the extent of OSA. In a closed-loop feedback system, a sensor that senses a physiological parameter associated with OSA (e.g., muscle or nerve electrical activity, tongue position, oropharyngeal airflow, etc.) can be utilized. More detailed descriptions of sensors that may be employed in a closed-loop system, as well as other examples of sensors and feedback control techniques that may be employed as part of the present disclosure are disclosed in U.S. Pat. No. 5,716,377.

Closed-Loop System

Figure 3:
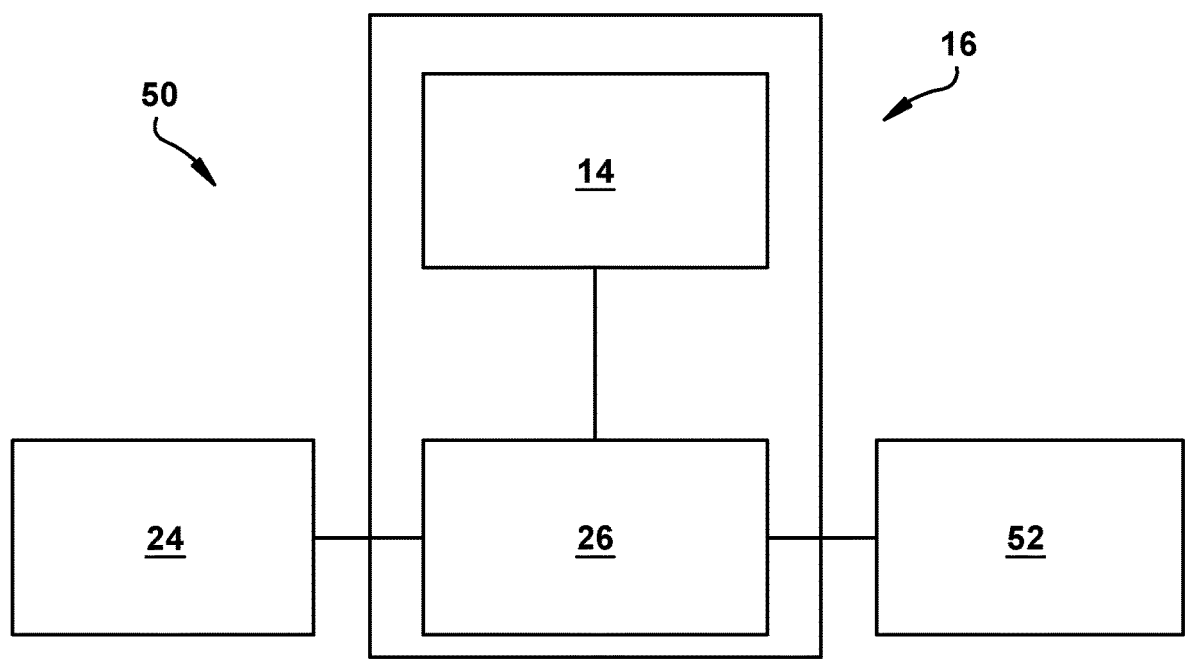
FIG. 3 is a schematic illustration of a closed-loop system for treating OSA according to another aspect of the present disclosure.

In another aspect, the present disclosure can include a closed-loop system 50 (FIG. 3) for treating OSA in a subject. The system 50 can comprise a power source 14, a neuromuscular stimulator 16, and a controller 26. The power source 14 and the neuromuscular stimulator 16 can be in direct and/or indirect electrical communication with one another. In some instances, the power source 14 and the neuromuscular stimulator 16 can be in direct electrical communication with one another via one or more wires (not shown). In other instances, the power source 14 and the neuromuscular stimulator 16 can be in indirect electrical communication with one another (e.g., via a wireless link). One or more components of the system 50 can be implantable in a subject suffering from OSA for a desired period of time (e.g., acute, semi-chronic, chronic). The system 50 can also be portable and adapted to be borne by a subject suffering from OSA for a desired period of time. In some instances, the system 50 can be borne by a subject for an acute period of time (e.g., during an emergency situation), for a semi-chronic period of time (e.g., less than about a week to about 6 weeks), or for a chronic period of time (e.g., greater than about 6 weeks). For example, the neuromuscular stimulator 16 can be temporarily or permanently implanted within, on, or otherwise associated with a subject suffering from OSA.

In another aspect, the power source 14 can be configured to deliver a therapy signal having certain power and stimulation parameters to the neuromuscular stimulator 16. Examples of such power and stimulation parameters can include the pulse waveform, the signal pulse width, the signal pulse frequency, the signal pulse phase, the signal pulse polarity, the signal pulse amplitude, the signal pulse intensity, and the signal pulse duration of the therapy signal. The power source 14 can be capable of conveying a variety of currents and voltages to the neuromuscular stimulator 16. In some instances, the power source 14 can communicate stimulating energy, such as electrical current pulses to the neuromuscular stimulator. The power source 14 can optionally include circuitry and/or other implantable components for outputting electrical pulses to the neuromuscular stimulator 16. Signals from the power source 14 can additionally or optionally be communicative in nature, for example, communicating stimulation program information, subject information, and other types of information. In some instances, the power source 14 is located external to the subject and in electrical communication with the neuromuscular stimulator 16 via inductive coupling. For example, the power source 14 can be configured as part of a wearable device, such as a chin strap (not shown), which may be worn at bedtime. In such instances, the power source 14 is not physically "wired" to the neuromuscular stimulator 16.

In another aspect, the neuromuscular stimulator 16 can include any active implantable medical device configured for implantation for a relatively short or long period of time. As discussed in more detail below, all or only a portion of the neuromuscular stimulator 16 can be configured for implantation on or in the mandible of a subject. For example, all or only a portion of the neuromuscular stimulator 16 can be configured for implantation on, in, or through a mandible 28 (e.g., the mentum 29) of the subject.

The controller 26 can be configured to receive the power and stimulation parameters associated with a therapy signal from the power source 14. In some instances, the controller 26 can include a microprocessor (not shown), a hardwired circuit (not shown), or other appropriate means for controlling various aspects of the system 50. For example, the controller 26 can operate the power source 14, convey therapy signals to at least one electrode 24, and/or receive information from various sources, such as the electrode or a sensing component 52. The controller 26 can be configured to store a stimulation program (or programs) and operate the power source 14 according to the stimulation program(s). Stimulation programs can include predetermined, set programs (e.g., hardwired into the controller) and adaptive, dynamic programs (e.g., software that adapts an artificial stimulation pattern according to various inputs). The controller 26 can select between various programs and/or actively modify a stimulation program according to various inputs, such as information received from a subject, information received from the sensing component 52, information received from the power source 14, information received from the at least one electrode 24, and/or information received from a health care provider.

In another aspect, the neuromuscular stimulator 16 can include one or more leads 22 (FIG. 4), each of which has at least one electrode 24 in electrical communication with the controller 26. The at least one electrode 24 can be configured to deliver a therapy signal to a target tissue associated with direct or indirect control of a posterior base of the tongue of a subject. In further describing representative electrodes 24, which are described in the singular, it will be apparent that more than one electrode may be used as part of the system 50. Accordingly, the description of a representative electrode 24 suitable for use in the system 50 of the present disclosure is applicable to other electrodes that may be employed.

The electrode 24 can include one or more of the following types and/or categories of electrodes: epimysial electrodes; intramuscular electrodes, such as Peterson electrodes; nerve cuff electrodes; self-contained electrodes; monopolar electrodes; bipolar electrodes; multi-contact electrodes; and/or other known electrode types/categories and combinations thereof. It will be appreciated that the electrode 18 can include one or more associated flexible, extensible electrical leads 22. The lead 22 and/or the electrode 24 can be highly flexible so as to not hinder regular tongue movement. In some instances, all or only a portion of the lead 22 can include one or more deployable anchoring elements (not shown) (e.g., barbs, hooks, etc.). The anchoring element(s) can be selectively retractable and extendable. The anchoring element(s) facilitate secure placement of the lead 22 (and thus the electrode 24) in or about a target tissue, such as a muscle, which is under constant flexion and relaxation.

The electrode 24 can be controllable to provide therapy signals that may be varied in voltage, frequency, pulsewidth, current and/or intensity. For example, the electrode 24 can also provide both positive and negative current flow from the electrode and/or be capable of stopping current flow from the electrode and/or changing the direction of current flow from the electrode. In some instances, the electrode 24 has the capacity for variable output, linear output and short pulse-width. In other instances, the electrode 24 can comprise a coil configured to deliver magnetic stimulation. The electrode 24 may be mono-polar, bipolar or multi-polar. To minimize the risk of an immune response triggered by the subject against certain components of the neuromuscular stimulator 16, and also to minimize damage thereto (e.g., corrosion from other biological fluids, etc.), the electrode 24 (and any wires and optional housing materials) can be made of inert materials, such as silicon, metal, plastic and the like. In other instances, the electrode 24 can be a multi-vector electrode capable of directing current to different muscles of anterior lingual musculature. In further instances, the system 50 can include more than one electrode 24, such as an array of electrodes to stimulate a field of arborizing hypoglossal branches associated with a particular target muscle (or group of muscles).

In another aspect, the system 50 also includes one or more sensing components 52 configured to detect at least one physiological parameter or a related symptom of OSA. The presence of the sensing component 52 enables closed-loop operation of the system 50 to treat OSA, meaning that treatment parameters (e.g., therapy signals) may be automatically adjusted in response to the sensed or detected physiological parameter or a related symptom of OSA. In some instances, the sensing component 52 and the electrode 24 can be the same structure or element. Advantageously, use of a single structure or element as the sensing component 52 and the electrode 24 reduces the invasive nature of the surgical procedure associated with implanting the system 50, while also reducing the number of foreign bodies introduced into a subject.

The sensing component 52 can be in direct and/or indirect electrical communication with the controller 26 and/or the power source 14 (e.g., via one or more leads 22 or a wireless link). In one example, the sensing component 52 can comprise a sensor (e.g., an electrode 24 as described above) that senses a physiological parameter or related symptom associated with OSA (e.g., muscle or nerve electrical activity, tongue position, oropharyngeal airflow, etc.). Examples of sensors that may be employed in a closed-loop system 50, as well as other examples of sensors and feedback control techniques that may be employed as part of the present disclosure are disclosed in U.S. Pat. No. 5,716,377.

The system 50 can be configured for highly selective stimulation and modulation of the anterior lingual musculature. In some instances, the system 50 can comprise multiple leads 22, each of which includes at least one electrode 24 and at least one sensing component 52. For example, the system 50 can have an "octopus-like" configuration whereby the tentacles correspond to the multiple leads 22 and the body corresponds to the neuromuscular stimulator 16. A distal end of each of the leads 22 can be configured for embedding into a pre-determined portion of a muscle comprising the anterior lingual musculature. The muscle(s) in which the distal ends of the leads 22 is/are embedded can be the same or different. Thus, in some instances, the distal ends of the leads 22 can be embedded in a single muscle but at different spatial locations. In such instances, the system 50 can be operated to activate (stimulate) a first portion of the muscle associated with a first lead (not shown), while simultaneously or sequentially inhibiting muscle function in a second different portion of the muscle associated with a second lead (not shown). Advantageously, a system 50 having a multiple-lead configuration provides highly selective control over targeted muscles of the anterior lingual musculature and, thus, the ability to therapeutically modulate the laryngeal introitus.

Figure 4:
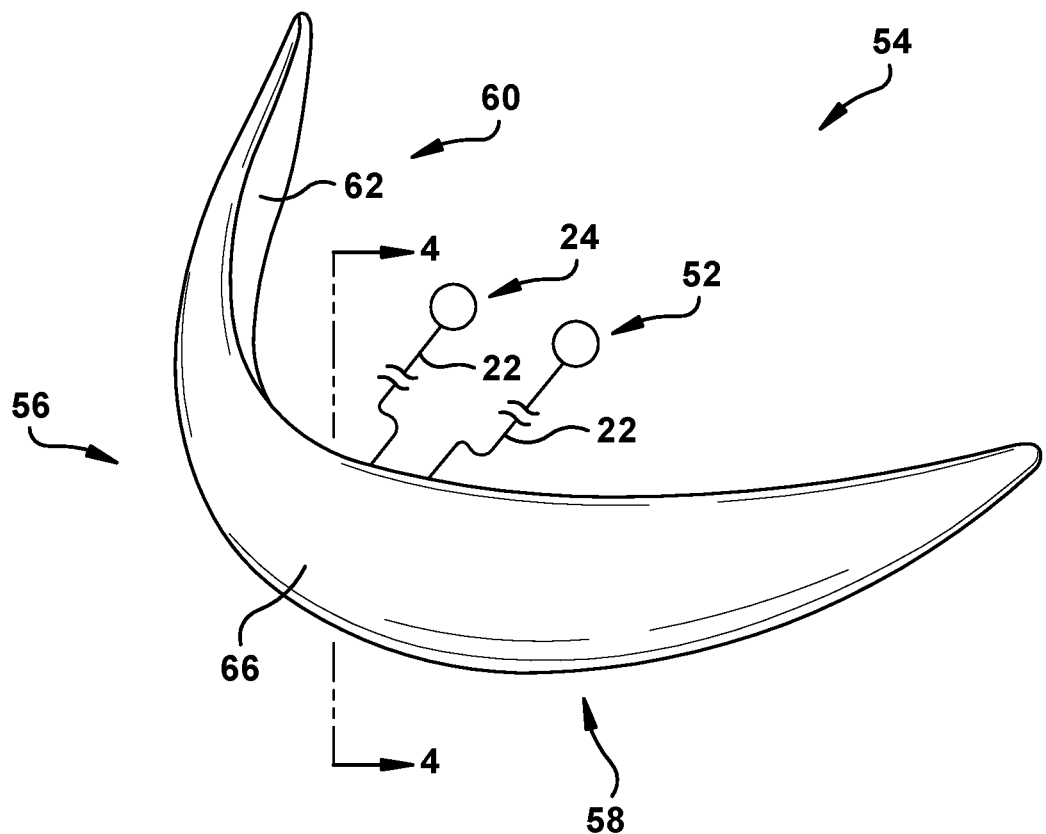
FIG. 4 is a perspective view of a system for treating OSA configured as a chin implant.
Figure 5:
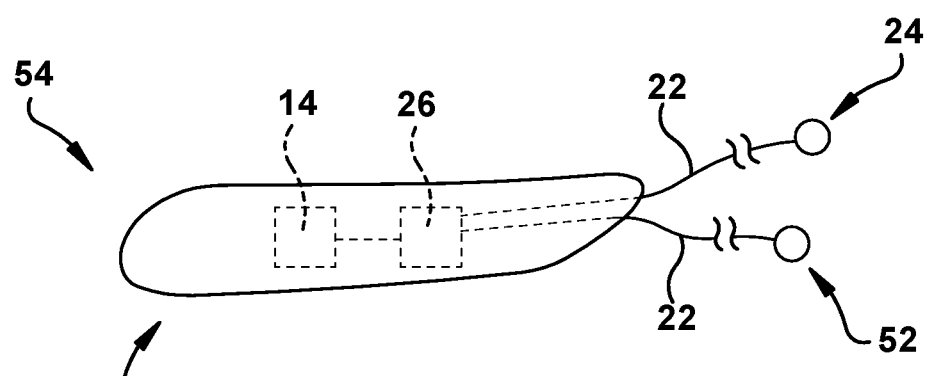
FIG. 5 is a cross-sectional view taken along Line 4-4 of the chin implant in FIG. 4.
Figure 6A:
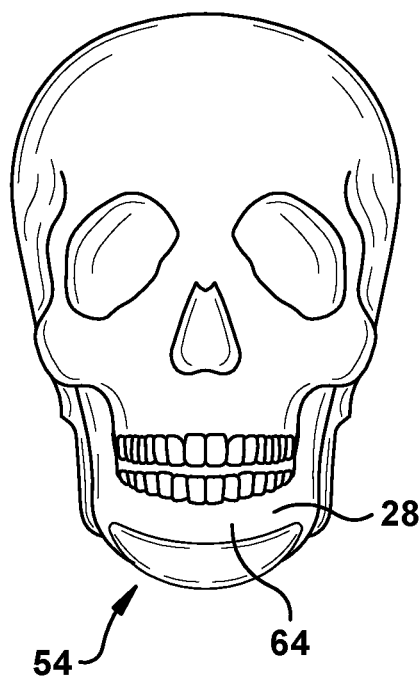
FIG. 6A is a frontal view of a human skull and mandible with the chin implant of FIG. 4 correctly positioned.
Figure 6B:
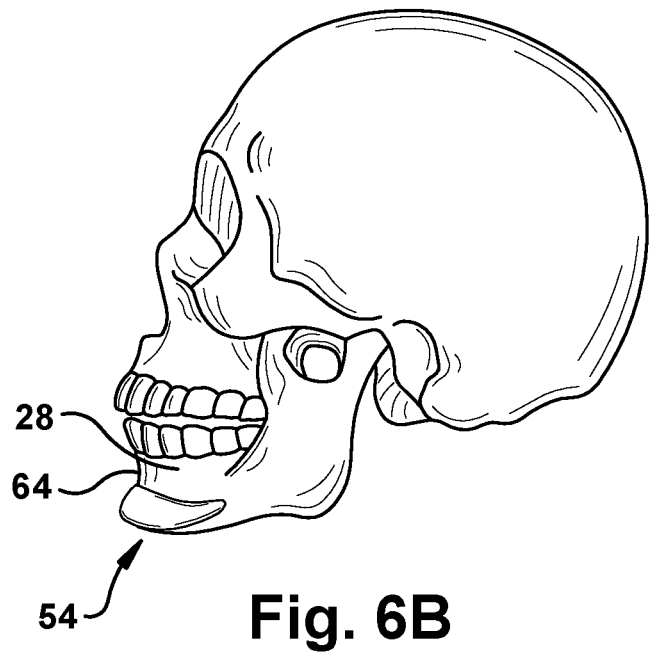
FIG. 6B is a profile view of the skull depicted in FIG. 6A.

One example of a system 50 for treating OSA is illustrated in FIGS. 4-6B. The system 50 can comprise a chin implant 54 for a human mandible 28 (FIGS. 6A-B). The chin implant 54 (FIG. 4) has a generally crescent-shaped configuration and, when implanted, gives the appearance of a natural chin contour. All or only a portion of the chin implant 54 can be made of one or more materials that is/are biologically inert and non-reactive to avoid infection in a subject's body (e.g., silicone and/or or plastic). By virtue of its construction, the chin implant 54 can be pliant, flexible and compressible.

As shown in FIGS. 4-5, the chin implant 54 can comprise an implant body 56, a controller 26, at least one electrode 24, a sensing component 52, and a power source 14. The implant body 56 can have a front face 58 and a back face 60. The back face 60 can have a surface 62 for placement adjacent the mental protuberance 64 of the mandible 28 (FIG. 6A). The front face 58 can have a curved projection surface 66 for protruding from the chin to create a natural chin profile after implantation (FIG. 6B). Each of the controller 26, the at least one electrode 24, the sensing component 52, and the power source 14 can be directly or indirectly associated with the implant body 56. As shown in FIG. 4, for example, the controller 26 and the power source 14 can be housed within a portion of the implant body 56, while the at least one electrode 24 and the sensing component 52 are located external to the implant body and directly connected to the controller (e.g., by leads 22). Although the power source 14 is shown as being disposed within the implant body 56, it will be appreciated that the power source may also be located external to the implant body (e.g., via a wireless link).

Methods

Figure 7:
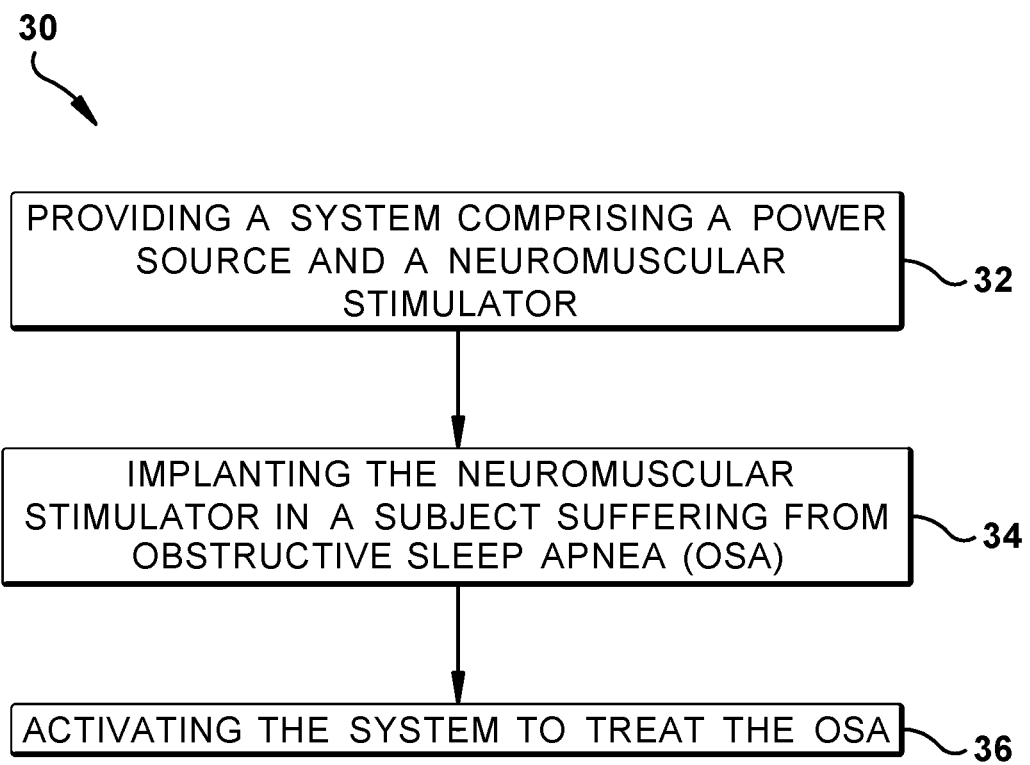
FIG. 7 is a process flow diagram illustrating a method for treating OSA according to another aspect of the present disclosure.

Another aspect of the present disclosure can include a method 30 (FIG. 7) for treating OSA in a subject. The method 30 can generally include the steps of providing a system 10 (Step 32), implanting a neuromuscular stimulator 16 of the system into a subject suffering from OSA (Step 34), and activating the system to treat the OSA (Step 36). The system 10 provided at Step 32 can be identically or similarly constructed as the system shown in FIG. 1 and described above. For the purpose of illustration only, the method 30 will be described below using the system 10 shown in FIG. 1.

At Step 34, the neuromuscular stimulator 16 can be implanted in the subject. In some instances, a trans-mandibular surgical approach can be used to implant the neuromuscular stimulator 16. A variety of trans-mandibular surgical approach options may be used, such as a submental approach or an intraoral bucca-gingival sulcus approach. Generally speaking, a submental approach allows for other adjunctive procedures including, but not limited to, cervical liposuction (e.g., for effacement of platysmal banding), elevation of hyoid positioning, and mandibular distal bone advancement for aesthetic purposes and/or functionally repositioning the anterior lingual musculature 12. Unlike the submental approach, an intraoral approach does not produce a facial scar. A trans-mandibular surgical approach can be performed under local anesthetic or in an outpatient setting; however, it will be appreciated that general anesthetic may alternatively be used as patients may be more comfortable and the patient's airway is better protected.

Figure 8:
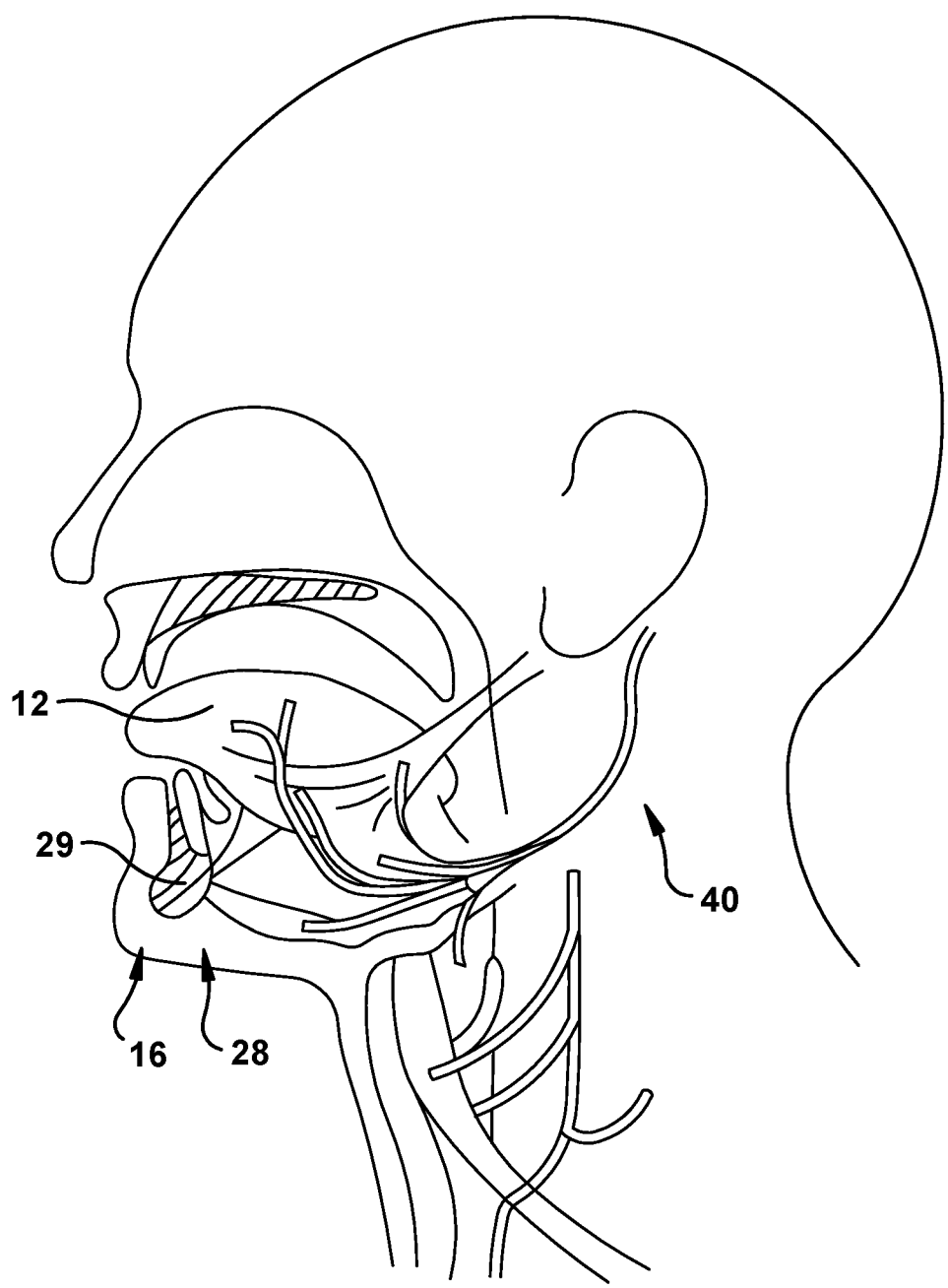
FIG. 8 is a schematic illustration showing the neuromuscular stimulator in FIG. 1 implanted in a subject.

Whether a submental or intraoral bucca-gingival sulcus approach is used, the dissection can be carried out to the level of the periosteum overlying the mentum 29 of the mandible 28 (FIG. 8). Surgical awareness is highlighted at this time in an effort to preserve and not traumatize the mental nerves (not shown). The mental nerves exit at the mid-vertical level of the mandible 28, between the region of the first and second pre-molars bilaterally. Like many surgeries in the head and neck, preservation of a nerve (or nerves) along with strict attention to hemostasis are key features of a successful operation. In making the gingivo-labial sulcus incision, for example, it can be important to leave an adequate cuff of mucosa along with a sufficient portion of the mentalis muscle (not shown) for later resuspension. Doing so can avoid lower-lip ptosis.

Figure 9:
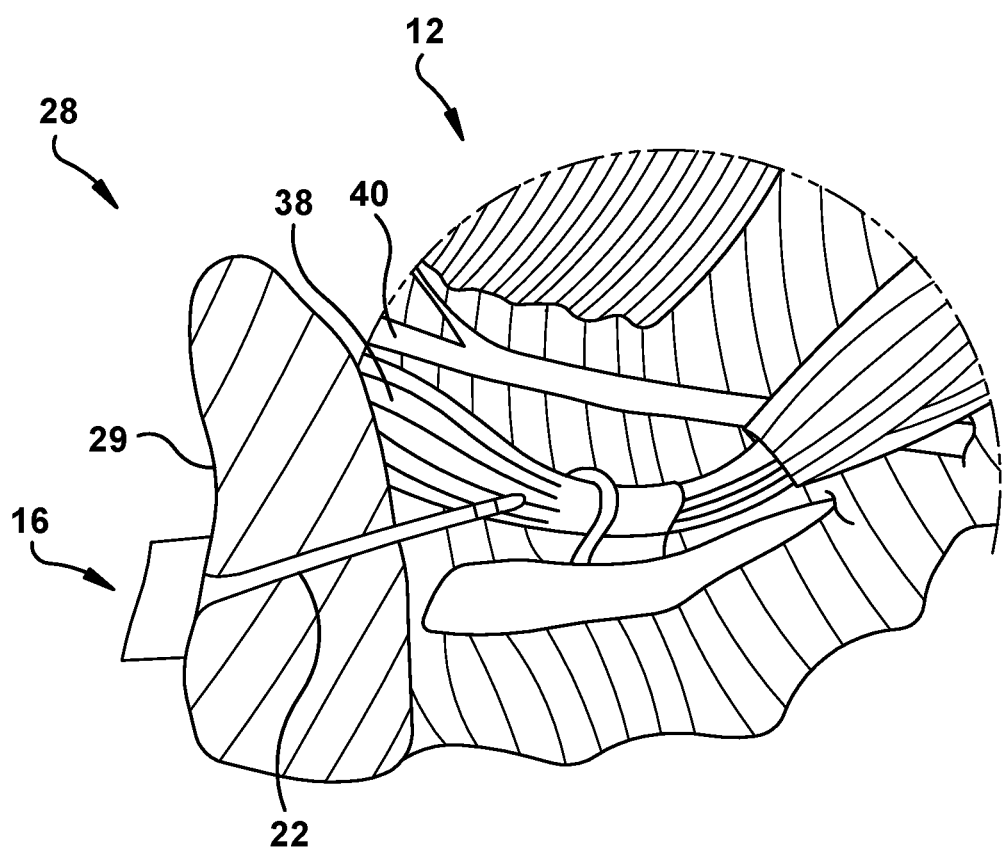
FIG. 9 is a schematic illustration showing a magnified view of the neuromuscular stimulator in FIG. 8.
Figure 10:
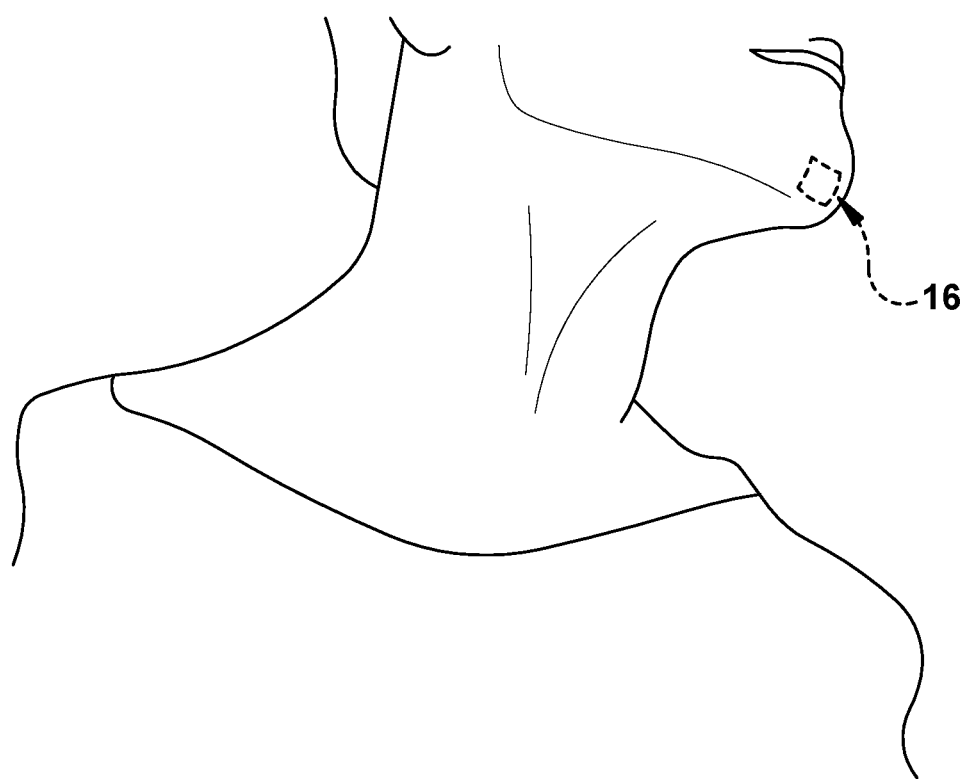
FIG. 10 is a schematic illustration showing the neuromuscular stimulator in FIG. 9 implanted in the subject.

FIGS. 8-10 illustrate a submental approach for implanting the neuromuscular stimulator 16 in a subject. First, an external submental crease incision (not shown) can be made. A subperiosteal dissection can then be made to elevate the periosteum and protect the mental nerves. At this point, a surgical mark can be made at the midline of the bony mentum 29. One or more drill holes (not shown) can be made above the inferior edge of the mentum 29, and on either side of the midline. For example, multiple drill holes can be made about 1 cm above the inferior edge of the mentum 29, and about 1.5 cm on either side of the midline. The diameter of each drill hole should be sufficient to pass the lead(s) 22 of the neuromuscular stimulator 16 through both cortices of the mandible 28 into electrical communication with one or more of the sublingual muscles that control the anterior positioning of the tongue base when contraction occurs.

In another example, an intraoral bucca-gingival sulcus approach can alternatively be used to implant the neuromuscular stimulator 16. Subperiosteal dissection can be carried out laterally to identify the mental nerves. The foramina (not shown) of the mental nerves are generally found between the first and second premolar teeth at the level of the origin of the mentalis muscle, or 2-4 mm below the level of the bicuspid premolar teeth apices. The foramina are situated deep to the midportion of the depressor anguli oris. Dissection can occur inferolaterally to allow for a longer osteotomy and thereby prevent unsightly mandibular notching. During dissection, the periosteum at the inferior rim of the mentum 29 can be left intact. Next, the skeletal midline can be aligned with the overlying soft tissue corollary. A sagittal saw with a 30-degree bend can then be used to facilitate an even cut while minimizing soft tissue trauma. Lateral cuts can be made about 4-5 mm below the foramina to compensate for the path of the inferior alveolar nerve.

In another variation of the method 30, the neuromuscular stimulator 16 can be configured to also serve as a chin implant. This may be desirable in instances where a subject desires an aesthetic change to their anterior mandibular profile. Alternatively, if a subject does not desire a change in their anterior mandibular profile, a relatively small or low-profile neuromuscular stimulator 16 that does not cause any profile changes can be used. For example, a neuromuscular stimulator 16 can be sized and dimensioned for placement within a drilled sulcus such that attachment of the neuromuscular stimulator therein does not interfere with the anterior mandibular profile of the subject.

Regardless of the trans-mandibular surgical approach used, the neuromuscular stimulator 16 can be implanted so that the electrode 24 is in electrical communication with a target tissue associated with control of a posterior base of the tongue of the subject (e.g., the electrode can be placed directly on and/or within the target tissue). In some instances, the electrode 24 can be placed into electrical communication with one or more muscles of the anterior lingual musculature 12. In other instances, two or more electrodes 24 can be placed bilaterally into electrical communication with one or more muscles of the anterior lingual musculature 12. In one example, the electrode 24 can be placed into electrical communication with a genioglossus muscle (not shown). In another example, the electrode 24 can be placed into electrical communication with an anterior belly digastric muscle 38 (FIG. 9). In another example, the electrode 24 can be placed into electrical communication with a hyoglossus muscle (not shown). In another example, the electrode 24 can be placed into electrical communication with a mylohyoid muscle (not shown).

Alternatively or additionally, the electrode 24 can be placed into electrical communication with a nerve (or nerves) that innervates one or muscles associated with control of a posterior base of the tongue of the subject, such as the hypoglossal nerve 40 and/or its distal arborizing branches at or near its neuromuscular junction. In some instances, the electrode 24 can be implanted directly in or on the target tissue. In other instances, the electrode can be implanted so that the electrode 24 is not in direct physical contact with the target tissue, but located in sufficient proximity to the target tissue such that delivery of a therapy signal to the electrode can modulate target tissue activity.

Proper positioning of the lead 22 can be confirmed by delivering test signals to the electrode 24 and then noting if the test signals result in anterior displacement of the posterior base of the tongue. Once the lead 22 is properly positioned, the housing 20 can be securely affixed to the subject. For example, the housing 20 can be securely affixed (e.g., with bone screws) into the external cortex of the mandible 28, or simply placed in a tight surgical subperiosteal pocket. Once the neuromuscular stimulator 16 is secured to the subject, the soft tissue can be closed in layers while paying special attention to the reattachment of the mentalis muscle to avoid ptotic lower lip. The soft tissue can then be re-draped with tape and the procedure completed (FIG. 10). Overall, the surgical implant procedure can take about 15 minutes to complete.

Figure 2:
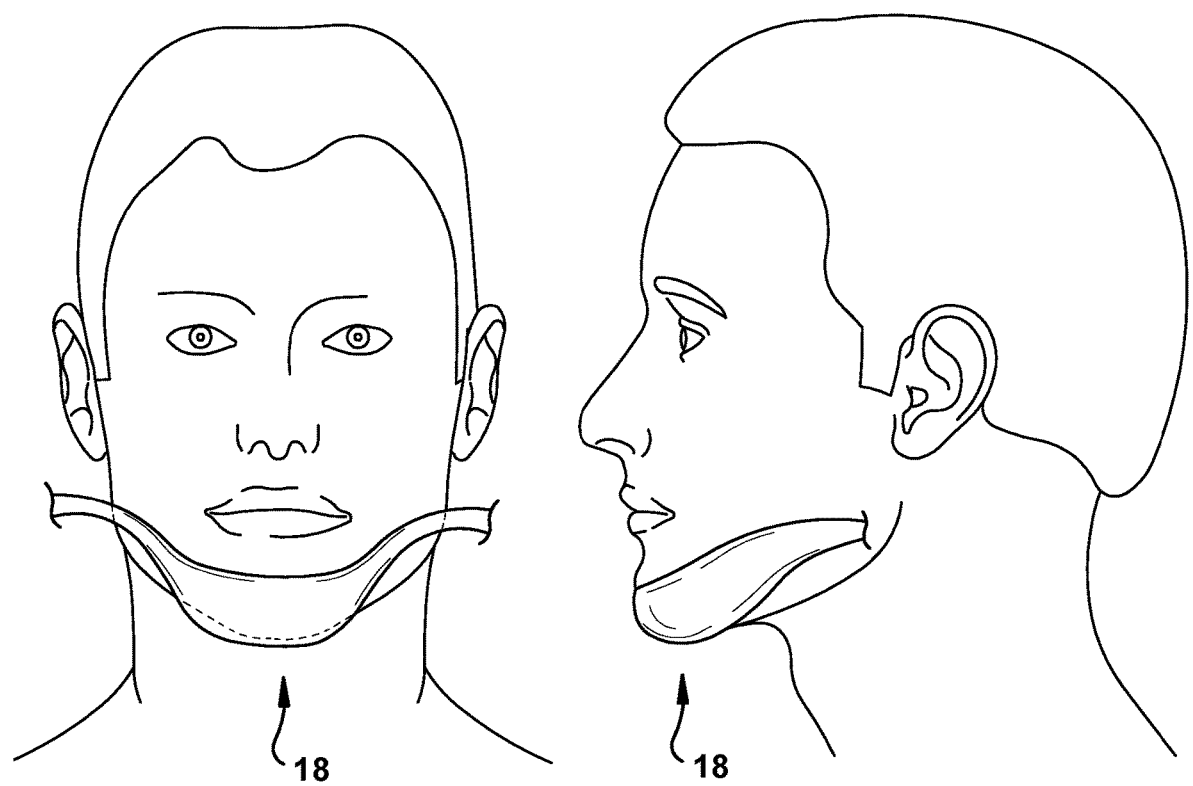
FIG. 2 is a schematic illustration showing a power source of the system in FIG. 1 configured as a chin strap.

At Step 34, the power source 14 can be associated with the subject (if it has not been done so already) so that the power source is in electrical communication with the neuromuscular stimulator 16. As shown in FIG. 2 and discussed above, for example, the power source 14 can be configured as a chin strap 18 and placed around the head of the subject.

With the neuromuscular stimulator 16 implanted in the subject, the power source 14 can be activated at Step 36. Activation of the power source 14 causes one or more therapy signals, having desired power and stimulation parameters, to be delivered to the neuromuscular stimulator 16. In some instances, the therapy signal(s) (e.g., an electrical signal) may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz, with a pulse-width of about 10 to about 1000 microseconds. The type of stimulation may vary and involve different waveforms known to the skilled artisan.

Depending upon the desired treatment regimen, the therapy signal(s) is/are relayed to the electrode 24. The therapy signal(s) can be relayed to the electrode 24 for a time and in an amount sufficient to displace the posterior base of the tongue in an anterior direction, which opens the oropharyngeal airway to the laryngeal introitus. Delivery of the therapy signal(s) to the target tissue can be done, for example, while the subject is sleeping. In patients with OSA, the posterior base of the tongue can fall backwards and obstruct breathing, especially when individuals lay flat on their backs. Therapy signal(s) from the neuromuscular stimulator 16 can be delivered to the target tissue on a continuous, periodic, or an as-needed basis to displace the posterior base of the tongue in an anterior direction (and/or change the surface morphology of the posterior tongue base to allow and increase oropharyngeal airway volume) while the subject is sleeping. This prevents obstruction of the airway during sleep by ensuring that airflow through the airway of the subject is properly maintained. Additionally or optionally, the therapy signal(s) can be relayed to the electrode 24 to achieve selective muscle activation; that is, targeted activation of less than all of the muscles comprising the anterior lingual musculature 12. Advantageously, selective stimulation of the anterior lingual musculature 12 can prevent or mitigate dysarthria.

Another aspect of the present disclosure can include a method 70 (FIG. 11) for treating OSA in a subject. The method 70 can generally include the steps of: providing a closed-loop system 50 (Step 72); implanting the system into a subject suffering from OSA (Step 74); generating a sensor signal based on a detected at least one physiological parameter or related symptom associated with OSA (Step 76); and delivering a therapy signal, by the system, to a target tissue to treat the OSA (Step 78). Steps 76-78 can be repeated for a desired period of time to treat the OSA (Step 80). The closed-loop system 50 provided at Step 72 can be identically or similarly constructed as the system shown in FIG. 3 and described above. For example, the system 50 shown in FIG. 3 can be configured to include multiple electrodes 24 and sensing components 52, which may limit total extrinsic and intrinsic tongue contraction and assist in anterior-superior elevation of the suprahyoid muscles (and thus the hyoid bone) to open the laryngeal introitus.

At Step 74, the system 50 can be implanted in the subject. In some instances, a trans-mandibular surgical approach can be used to implant the system 50. A variety of trans-mandibular surgical approach options may be used, such as a submental approach or an intraoral bucca-gingival sulcus approach. Generally speaking, a submental approach allows for other adjunctive procedures including, but not limited to, cervical liposuction (e.g., for effacement of platysmal banding), elevation of hyoid positioning, and mandibular distal bone advancement for aesthetic purposes and/or functionally repositioning the anterior lingual musculature. Unlike the submental approach, an intraoral approach does not produce a facial scar. A trans-mandibular surgical approach can be performed under local anesthetic or in an outpatient setting; however, it will be appreciated that general anesthetic may alternatively be used as patients may be more comfortable and the patient's airway is better protected.

Whether a submental or intraoral bucca-gingival sulcus approach is used, the dissection can be carried out to the level of the periosteum overlying the mentum of the mandible 28. Surgical awareness is highlighted at this time in an effort to preserve and not traumatize the mental nerves (not shown). The mental nerves exit at the mid-vertical level of the mandible, between the region of the first and second pre-molars bilaterally. Like many surgeries in the head and neck, preservation of a nerve (or nerves) along with strict attention to hemostasis are key features of a successful operation. In making the gingivo-labial sulcus incision, for example, it can be important to leave an adequate cuff of mucosa along with a sufficient portion of the mentalis muscle (not shown) for later resuspension. Doing so can avoid lower-lip ptosis.

In one example, a submental approach can be used to implant the system 50 in a subject suffering from OSA. First, an external submental crease incision (not shown) can be made. A subperiosteal dissection can then be made to elevate the periosteum and protect the mental nerves. At this point, a surgical mark can be made at the midline of the bony mentum. One or more drill holes (not shown) can be made above the inferior edge of the mentum, and on either side of the midline. For example, multiple drill holes can be made about 1 cm above the inferior edge of the mentum, and about 1.5 cm on either side of the midline. The diameter of each drill hole should be sufficient to pass the leads 22 associated with the at least one electrode 24 and the sensing component 52 of the system 50 through both cortices of the mandible 28 into electrical communication with first and second target tissues, respectively.

In another example, an intraoral bucca-gingival sulcus approach can alternatively be used to implant the system 50. Subperiosteal dissection can be carried out laterally to identify the mental nerves. The foramina (not shown) of the mental nerves are generally found between the first and second premolar teeth at the level of the origin of the mentalis muscle, or 2-4 mm below the level of the bicuspid premolar teeth apices. The foramina are situated deep to the midportion of the depressor anguli oris. Dissection can occur inferolaterally to allow for a longer osteotomy and thereby prevent unsightly mandibular notching. During dissection, the periosteum at the inferior rim of the mentum can be left intact. Next, the skeletal midline can be aligned with the overlying soft tissue corollary. A sagittal saw with a 30-degree bend can then be used to facilitate an even cut while minimizing soft tissue trauma. Lateral cuts can be made about 4-5 mm below the foramina to compensate for the path of the inferior alveolar nerve.

The foregoing surgical approaches can include implantation of a chin implant 54 (such as the one described above) in instances where a subject desires an aesthetic change to their anterior mandibular profile. Alternatively, if a subject does not desire a change in their anterior mandibular profile, a relatively small or low-profile neuromuscular stimulator 16 that does not cause any profile changes can be used. For example, a neuromuscular stimulator 16 can be sized and dimensioned for placement within a drilled sulcus such that attachment of the neuromuscular stimulator therein does not interfere with the anterior mandibular profile of the subject.

Regardless of the trans-mandibular surgical approach used, the system 50 can be implanted so that the electrode 24 and the sensing component 52 are in electrical communication with first and second target tissues, respectively (e.g., the electrodes can be placed directly on and/or within the first and second target tissue). The first and second target tissues can be the same or different. In some instances, the electrode 24 can be placed into electrical communication with a first target tissue comprising one or more muscles of the anterior lingual musculature 12 (e.g., one or a combination of suprahyoid muscles). In one example, the electrode 24 and/or the sensing component 52 can be placed into electrical communication with a genioglossus muscle (not shown). In another example, the electrode 24 and/or the sensing component 52 can be placed into electrical communication with an anterior belly digastric muscle (not shown). In another example, the electrode 24 and/or the sensing component 52 can be placed into electrical communication with a hyoglossus muscle (not shown). In another example, the electrode 24 and/or the sensing component 52 can be placed into electrical communication with a mylohyoid muscle (not shown).

Proper positioning of the electrode 24 can be confirmed by delivering test signals to the electrode and then noting if the test signals result in anterior displacement of the posterior base of the tongue. Once the electrode 24 is properly positioned, the remainder of the system 50 can be securely affixed to the subject. For example, the implant body 56 of a chin implant 54 can be securely affixed (e.g., with bone screws) into the external cortex of the mandible 28. Once the system 50 is securely implanted in the subject, the soft tissue can be closed in layers while paying special attention to the reattachment of the mentalis muscle to avoid ptotic lower lip. The soft tissue can then be re-draped with tape and the procedure completed. Overall, the surgical implant procedure can take about 15 minutes to complete.

If it has not been done so already, the power source 14 can be associated with the subject so that the power source is in electrical communication with the neuromuscular stimulator 16. With the system 50 implanted in the subject, the power source 14 can then be activated. Activation of the power source 14 enables the sensing component 52 to detect at least one physiological parameter or a related symptom associated with OSA. Activation of the power source 14 also permits one or more therapy signals having desired power and stimulation parameters to be delivered to the electrode 24. In some instances, the therapy signal(s) (e.g., an electrical signal) may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz, with a pulse-width of about 10 to about 1000 microseconds. The type of stimulation may vary and involve different waveforms known to the skilled artisan.

At Step 76, a sensor signal can be generated by the sensing component 52 in response to at least one physiological parameter or a related symptom associated with OSA detected by the sensing component. Where the sensing component 52 is an EMG electrode, for example, the activity of one or more muscles of the anterior lingual musculature (e.g., a genioglossus muscle or a suprahyoid muscle) can be detected. A detected decrease in muscle activity (relative to a control or baseline level) may cause the sensing component 52 to generate a corresponding sensor signal, which is then relayed to the controller 26 and/or the power source 14.

In response to the generated sensor signal, the system 50 can cause a therapy signal (or signals) to be delivered to the electrode 24 (Step 78). The controller 26 can then control operation of the neuromuscular stimulator to adjust application of the therapy signal(s) to the first target tissue in response to the sensor signal. For example, the therapy signal(s) can be relayed to the electrode 24 for a time and in an amount sufficient to displace the posterior base of the tongue in an anterior direction, which opens the oropharyngeal airway to the laryngeal introitus. Delivery of the therapy signal(s) to the target tissue can be done, for example, while the subject is sleeping. In patients with OSA, the posterior base of the tongue can fall backwards and obstruct breathing, especially when individuals lay flat on their backs. Therapy signal(s) from the neuromuscular stimulator 16 can be delivered to the first target tissue on a continuous, periodic, or an as-needed basis to displace the posterior base of the tongue in an anterior direction (and/or change the surface morphology of the posterior tongue base to allow and increase oropharyngeal airway volume) while the subject is sleeping. This prevents obstruction of the airway during sleep by ensuring that airflow through the airway of the subject is properly maintained. Additionally or optionally, the therapy signal(s) can be relayed to the electrode 24 to achieve selective muscle activation; that is, targeted activation of less than all of the muscles comprising the anterior lingual musculature. Advantageously, selective stimulation of the anterior lingual musculature can prevent or mitigate dysarthria. It will be appreciated that although the method 70 is described in terms of unilateral stimulation, the method can also be performed using bilateral stimulation (e.g., stimulating two muscles simultaneously or in sequence).

Figure 11:
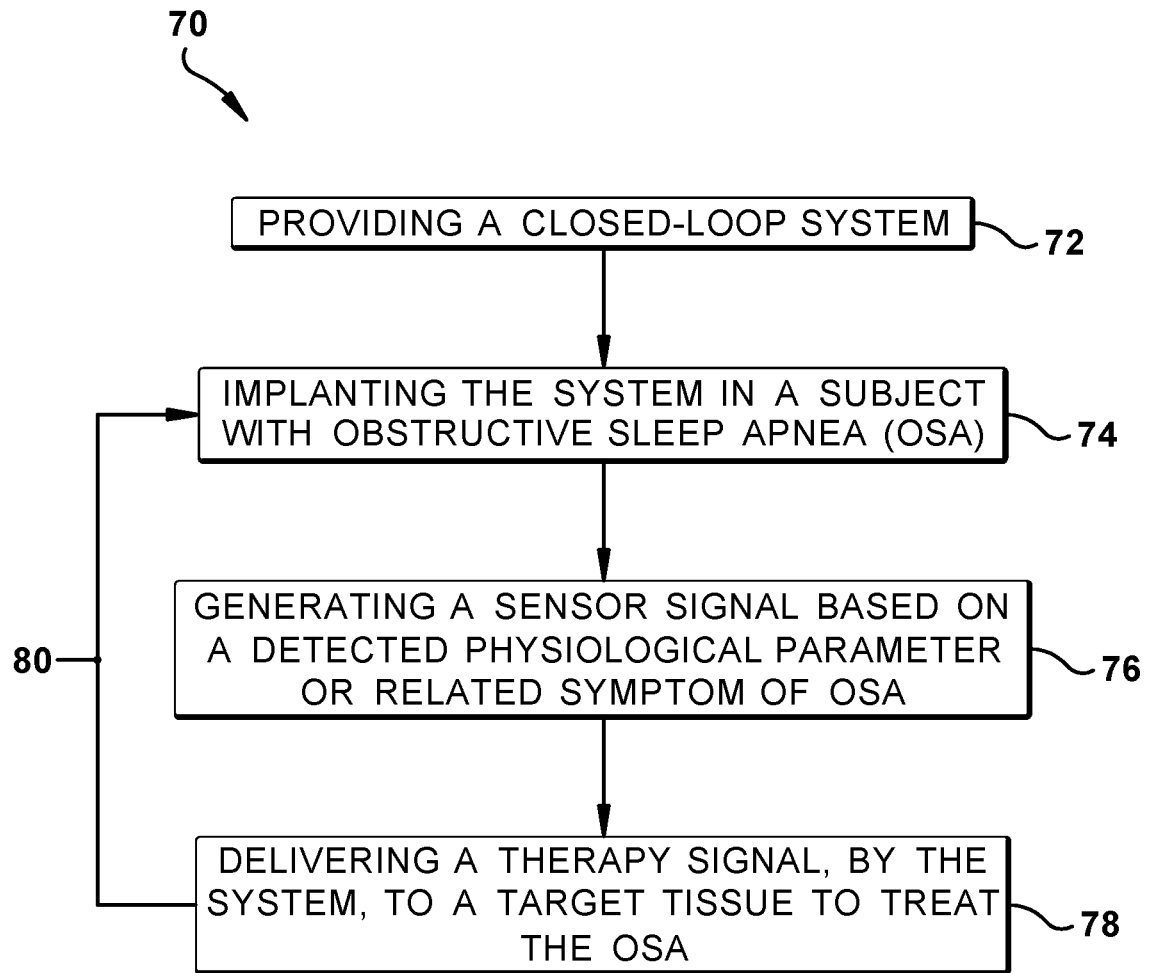
FIG. 11 is a process flow diagram illustrating a method for treating OSA in a subject according to another aspect of the present disclosure.

As shown in FIG. 11, Steps 76-78 can be repeated for a period of time to treat the OSA. Advantageously, the method 70 provides a minimally invasive, automatic, and aesthetically acceptable treatment modality for OSA that is continually titrated to optimize its efficacy based on continuous physiological feedback, thereby enabling a high degree of patient-specific customization.

It will be appreciated that the present disclosure may also be an adjunct to other mechanical orthognathic maneuvers to sections of the mandible that have tongue muscle attachments to them.

From the above description of the present disclosure, those skilled in the art will perceive improvements, changes and modifications. For example, it will be appreciated that a subject may be placed in a sleep lab after surgery so that particular settings (e.g., stimulation parameters) of the system 10 and 50 can be optimized based on the needs of the subject. Additionally, it will be appreciated that, depending upon the static placement of the sublingual muscles, a preoperative decision can be made (e.g., based on soft and hard tissue cephalometrics) to reposition the anterior mentum and lingual muscle attachments to statically permit further advancement of the tongue base in concert with electrical stimulation of the sublingual muscles. Such improvements, changes, and modifications are within the skill of those in the art and are intended to be covered by the appended claims. All patents, patent applications, and publication cited herein are incorporated by reference in their entirety.

The following is claimed:

1. A device for improving disordered breathing that occurs during sleep in a subject, the device comprising:
    an implantable stimulator including a controller;
    a first elongate electrical lead connected to the stimulator, the first lead including a first electrode in electrical communication with the controller, wherein the first lead is configured to be positioned at a first portion of a lingual muscle; and
    a second elongate electrical lead connected to the stimulator, the second lead comprising a second electrode in electrical communication with the controller, wherein the second lead is configured to be positioned at a second portion of the lingual muscle spaced apart from the first portion,
    wherein, when the device is implanted in the subject, the controller is configured deliver a therapy signal to the first and second electrodes to stimulate distal arborizing branches of the hypoglossal nerve that are proximate the lingual muscle to improve the subject's disordered breathing that occurs during sleep.

2. The device of claim 1, wherein the first lead includes an anchoring element configured to secure the first lead to local tissue while implanted.

3. The device of claim 2, wherein the anchoring element is a first anchoring element and the second lead includes a second anchoring element configured to secure the second lead to local tissue while implanted.

4. The device of claim 1, wherein both the first lead and the second lead extend in substantially the same direction.

5. The device of claim 1, wherein the implantable stimulator is configured to be powered by an external power source via inductive coupling.

6. The device of claim 1, wherein the lingual muscle is the genioglossus muscle.

7. The device of claim 1, wherein, when the device is implanted in the subject, one or both of the first and second electrodes is configured to sense a physiological parameter.

8. The device of claim 7, wherein the physiological parameter is electrical activity of the lingual muscle.

9. The device of claim 7, wherein the physiological parameter is tongue position.

10. The device of claim 7, wherein the physiological parameter is oropharyngeal airflow.

11. A device for improving disordered breathing that occurs during sleep in a subject, the device comprising:
    an implantable stimulator including a controller;
    a first elongate electrical lead connected to the stimulator and in electrical communication with the controller, wherein the first lead is configured to be positioned at a first portion of a lingual muscle;
    a second elongate electrical lead connected to the stimulator and in electrical communication with the controller, wherein the second lead is configured to be positioned at a second portion of the lingual muscle spaced apart from the first portion; and a plurality of electrodes disposed on the first and second leads and configured to be positioned proximate distal arborizing branches of the hypoglossal nerve when the first and second leads are positioned at the first and second portions of the lingual muscle, wherein, when the device is implanted in the subject, the device is configured to stimulate the distal arborizing branches of the hypoglossal nerve via the electrodes to improve the subject's disordered breathing that occurs during sleep.

12. The device of claim 11, wherein the first lead includes an anchoring element configured to secure the first lead to local tissue while implanted.

13. The device of claim 12, wherein the anchoring element is a first anchoring element and the second lead includes a second anchoring element configured to secure the second lead to local tissue while implanted.

14. The device of claim 11, wherein both the first lead and the second lead extend in substantially the same direction.

15. The device of claim 11, wherein the implantable stimulator is configured to be powered by an external power source via inductive coupling.

16. The device of claim 11, wherein the lingual muscle is a genioglossus muscle.

17. The device of claim 11, wherein, when the device is implanted in the subject, at least one of the plurality of electrodes is configured to sense a physiological parameter.

18. The device of claim 17, wherein the physiological parameter is electrical activity of the lingual muscle.

19. The device of claim 17, wherein the physiological parameter is tongue position.

20. The device of claim 17, wherein the physiological parameter is oropharyngeal airflow.

* * * * *